(12) United States Patent
Kuzma et al.

(10) Patent No.: US 6,304,787 B1
(45) Date of Patent: Oct. 16, 2001

(54) COCHLEAR ELECTRODE ARRAY HAVING CURRENT-FOCUSING AND TISSUE-TREATING FEATURES

(75) Inventors: Janusz A. Kuzma, Englewood, CO (US); William Vanbrooks Harrison, Valencia; Albert A. Maltan, Stevenson Ranch, both of CA (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/375,424

(22) Filed: Aug. 17, 1999

Related U.S. Application Data

(63) Continuation-in-part of application No. 09/247,734, filed on Feb. 9, 1999, now Pat. No. 6,129,753, which is a continuation-in-part of application No. 09/140,034, filed on Aug. 26, 1998, now Pat. No. 6,038,484.
(60) Provisional application No. 60/101,942, filed on Sep. 25, 1998.

(51) Int. Cl.[7] ....................................................... A61N 1/36
(52) U.S. Cl. ........................................... 607/137; 607/115
(58) Field of Search .................................... 607/115, 137, 607/136, 116, 117

(56) References Cited

U.S. PATENT DOCUMENTS

| | | | |
|---|---|---|---|
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 4,991,582 | 2/1991 | Byers et al. | 128/419 |
| 5,000,194 | 3/1991 | van den Honert et al. | 128/784 |
| 5,037,497 | 8/1991 | Stypulkowski | 156/245 |
| 5,443,493 | 8/1995 | Byers et al. | 607/137 |
| 5,545,219 | 8/1996 | Kuzma | 623/10 |
| 5,578,084 | 11/1996 | Kuzma et al. | 623/10 |
| 5,603,726 | 2/1997 | Schulman et al. | 607/57 |
| 5,645,585 | 7/1997 | Kuzma | 623/10 |
| 5,649,970 | 7/1997 | Loeb et al. | 607/57 |
| 5,653,742 | 8/1997 | Parker et al. | 607/137 |
| 5,667,514 | 9/1997 | Heller | 606/108 |
| 5,776,178 | * | 7/1998 | Pohndorf et al. . |
| 5,929,041 | 7/1999 | Magal | 514/4 |

FOREIGN PATENT DOCUMENTS

| | | |
|---|---|---|
| 9631087 | 3/1996 | (WO) . |
| 9729802 | 8/1997 | (WO) . |
| 9922806 | 5/1999 | (WO) . |

* cited by examiner

*Primary Examiner*—Scott M. Getzow
(74) *Attorney, Agent, or Firm*—Bryant R. Gold

(57) ABSTRACT

An implantable electrode array, adapted for insertion into a cochlea, provides a multiplicity of exposed electrode contacts, each having a shape, geometry, or makeup that aids in controlling the current flow and current density associated with the electrode contact as a function of position on the electrode contact. In one embodiment, the shape or geometry of the exposed electrode contact controls the contact surface of the electrode contact in a way that varies the current flow and current density as a function of surface area position on the electrode, thereby focusing most of the current to flow through the center of the electrode contact. In another embodiment, the electrode contact is coated with a dielectric or other material that controls the surface contact impedance as a function of distance from the center of the electrode, again focusing most of the current flow through the center of the electrode contact. In yet a further embodiment, the exposed electrode contact surface area is masked with an insulator to prevent conduction of current at various locations on the surface of the electrode contact. Separately, or in combination with any of the above embodiments, the exposed electrode contact surface and/or the entire electrode array may be coated with a selected substance or drug compound that diffuses into the tissue and liquids surrounding the electrode. Such substance or drug compound is selected to elicit a desired result, e.g., to inhibit fibrous tissue or bone growth in the vicinity of the electrode contacts; to promote healing of damaged tissue in the region of the electrode contacts, to prevent neural degeneration, or to promote neural regeneration.

17 Claims, 13 Drawing Sheets

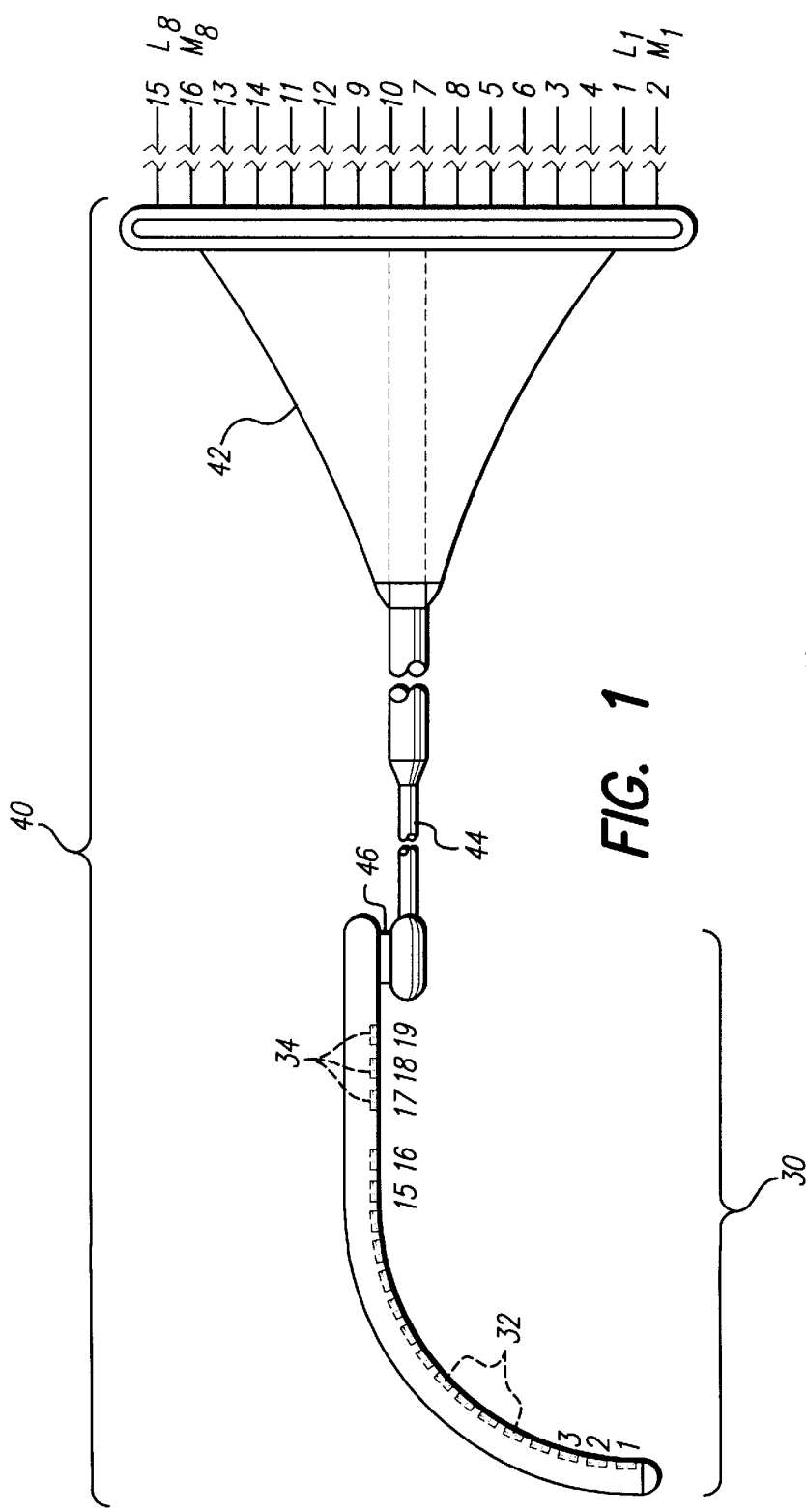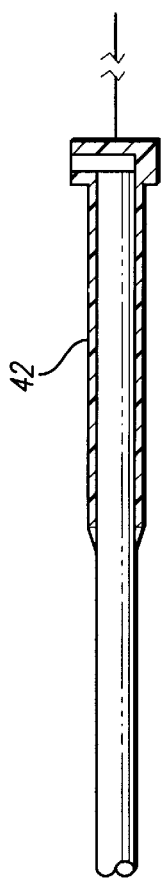
FIG. 1
FIG. 2

COCHLEAR ELECTRODE ARRAY HAVING CURRENT-FOCUSING AND TISSUE-TREATING FEATURES

This application is a continuation-in-part (CIP) application of U.S. application Ser. No. 09/247,734, filed Feb. 9, 1999 now U.S. Pat. No. 6,129,753, which is a continuation-in-part (CIP) of U.S. application Ser. No. 09/140,034, filed Aug. 26, 1998 now U.S. Pat. No. 6,038,484, all of which patent applications are incorporated herein by reference. This application further claims the benefit of U.S. Provisional Application Ser. No. 60/101,942, filed Sep. 25, 1998, also incorporated herein by reference.

BACKGROUND OF THE INVENTION

The present invention relates to an electrode array for use with a cochlear stimulator. More particularly, the present invention relates to an electrode array that: (1) uses geometrically shaped and/or treated electrode contacts to better steer or focus the electrical stimulation current to desired target tissue; and (2) uses coatings of a selected drug(s) or compound(s) on the electrical contacts (or spread over the entire electrode array) to promote a desired therapeutic treatment of the tissue in the vicinity of the electrode array, e.g., to inhibit growth of fibrous tissue or bone tissue, to promote healing, to prevent neural degeneration, and/or to promote neural regeneration.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea (the hair cells are located in the vicinity of the radially outer wall of the cochlea) by presenting electrical stimulation to the auditory nerve fibers directly, leading to the perception of sound in the brain and at least partial restoration of hearing function. The common denominator in most of these cochlear prosthesis systems has been the implantation into the cochlea of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrode contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall so that the stimulation current flowing from or to the electrode contacts can effectively stimulate the ganglion cells.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference.

Applicant's related patent applications, referenced above, also disclose a preferred approach for achieving an electrode array that hugs the modiolar wall of the scala tympani. The teachings of those patent applications, repeated in large part herein, are also applicable to the present invention.

The geometry of the electrode contacts provided by traditional cochlear electrodes, i.e., the shape of the exposed electrode contact, has heretofore been determined primarily by the need to place the electrode in certain locations within the tissue where the electrode is to be implanted. Disadvantageously, the concentration of current densities associated with such traditionally-shaped electrodes has not always been optimized to concentrate current flow in the target tissue area. Hence, there is a need for a cochlear electrode array wherein the electrode contacts themselves are designed to better steer or focus the stimulation current to the target tissue.

One exception to the traditional approach of electrode contacts is disclosed in U.S. Pat. No. 5,649,970, incorporated herein by reference. However, the approach shown in the '970 patent, while quite effective at achieving its intended purpose, is difficult and expensive to manufacture.

Further, it is noted that when the electrode array is first inserted into the scala tympani, and thereafter, there may be a need to treat the tissue in the surrounding area with an appropriate drug or other compound in order to, e.g., inhibit the growth of fibrous tissue, inhibit the growth of bone tissue, promote healing, prevent neural degeneration, and/or promote neural regeneration. Other than applicant Kuzma's provisional patent application, Ser. No. 60/101,942, filed Sep. 25, 1998, referenced above, applicants are not aware of any cochlear electrode designs that address this need to apply therapeutic drugs or other compounds to the target cochlear tissue.

It is thus evident that improvements are still needed in cochlear electrodes, particularly to facilitate assembling an electrode so that the electrode contacts are on the medial side of the electrode array, to better assure that the electrode assumes a close hugging relationship with the modiolus once implantation of the electrode has occurred, to enhance the ability of the electrode to better direct or focus the current density flowing to/from the electrode contacts at the target tissue, and/or to provide ways to apply therapeutic drugs or other compounds to the target tissue at the same time that electrical stimulation is provided to the target tissue.

SUMMARY OF THE INVENTION

The present invention addresses the above and other needs by providing a universal electrode array, adapted for insertion into either a left or right cochlea, which provides improved stability of electrode contact direction. All of the electrode contacts are spaced apart along one edge or side of the array, termed the "medial side". The structure of the electrode array facilitates bending of the array with the electrode contacts on the inside of the bend, yet deters flexing or twisting of the array that would tend to position or point the electrode contacts away from the inside of the bend. Hence, when inserted into the scala tympani duct of a cochlea, all of the electrode contacts on the medial side of the array generally face the modiolus wall of the cochlea.

In accordance with one important aspect of the present invention, the exposed electrode contacts on the surface of the electrode array have a shape, geometry, or makeup that aids in controlling the current flow and current density associated with the electrode contact as a function of position on the electrode contact. For example, in one embodiment of the invention, the shape or geometry of the exposed electrode contacts is designed to diminish the surface of the electrode contact at the outside edges of the contact, thereby focusing most of the current to flow through the center of the electrode contact. In another embodiment, the electrode contact is coated with a dielectric or other material so that the surface contact impedance increases as a function of distance from the center of the electrode, again focusing most of the current flow through the center of the electrode contact. In yet a further embodiment, the exposed electrode contact surface area is masked with a suitable insulator to prevent conduction of current at various locations at the electrode contact edge or at other areas on the exposed surface.

In accordance with another important aspect of the invention, the exposed electrode contact surface and/or the entire electrode array, is coated with a selected substance or compound, e.g., a drug, that diffuses into the tissue and liquids surrounding the electrode. Such substance or compound is used to elicit a desired therapeutic or other result, e.g., to inhibit fibrous tissue or bone growth in the vicinity of the electrode contacts; or to promote healing of damaged tissue in the region of the electrode contacts, or to prevent neural degeneration and/or to promote neural regeneration. In addition coating the array and/or electrode contact with such substance or compound when the electrode array is first implanted, additional substances or compounds may advantageously be delivered through a delivery channel that forms part of the electrode array, as taught, e.g., in applicant Kuzma's copending U.S. patent application Ser. No. 09/375,425, filed concurrently herewith, entitled "Cochlear Electrode With Drug Delivery Channel, and Method of Making Same", which patent application is assigned to the same assignee as is the present application, and which patent application is incorporated herein by reference. Representative substances or compounds that may be used to coat the electrode array and/or the individual electrode contacts in accordance with this aspect of the invention include selected steroids, either naturally occurring or synthetic, or a Neurotrophin selected to prevent neural degeneration and/or to promote neural regeneration.

Advantageously, the electrode array of the present invention can be manufactured using easy, low cost technology; and once made can be easily inserted, removed and reinserted, if required, into the cochlea or other curved body cavity.

In one embodiment, small non-conductive bumps or humps are formed in the carrier between the electrode contact areas on the medial side of the array. These small bumps are made, e.g., from a soft silicone rubber, or equivalent substance. When inserted into the cochlea, the small bumps serve as non-irritating stand-offs, or spacers, that keep the electrode contacts near the modiolus wall, but prevent the electrode contacts from actually touching the modiolus wall. The bumps further serve as dielectric insulators that form a compartment around each electrode contact, which compartment helps steer the stimulating electrical current in the desired direction, towards the modiolus wall, as taught, e.g., in copending U.S. patent application Ser. No. 09/137,033, filed Aug. 28, 1998, assigned to the same assignee as the present application, and incorporated herein by reference.

Once the electrode array of the present invention, with its electrode contacts all facing the modiolus wall, has been inserted into the cochlea, a flexible positioner may be inserted behind the electrode array so as to force the electrode contacts up against the modiolus wall. The description and use of such a positioner is not the subject of the present application, but is described in Applicant's copending patent applications, Ser. No. 09/140,034, filed Aug. 26, 1998 and Ser. No. 09/216,063, filed Dec. 18, 1998, both of which applications are assigned to the same assignee as is the present application , and both of which are incorporated herein by reference. However, it is to be understood that although the positioner described in the subject patent applications may be used with the electrode array of the present invention, the electrode array herein described is not limited to use with such a positioner. Rather, because the electrode array described herein offers current steering and drug coating advantages, and will most often have its electrode contacts facing in the medial direction without concern for twisting of the carrier (and hence without concern for having the electrode contacts pointing away from the medial direction), the electrode array offers advantages by itself not heretofore available with prior art electrode arrays.

Insertion of the electrode array into the cochlea may be performed in conventional manner, e.g., using the electrode insertion tool described in U.S. Pat. No. 5,443,493, incorporated herein by reference. Equivalent or similar insertion tools may also be used, such as that taught in U.S. patent application Ser. No. 09/313,901, filed May 18, 1999, also incorporated herein by reference.

Advantageously, the electrode array of the present invention achieves the following goals: (1) it helps assure that the electrode contacts of the electrode array will be optimally positioned facing the medial direction, e.g., facing the modiolar wall in a cochlea of any size or any side (left or right) of the body; (2) it can be manufactured using easy, low cost technology; (3) it can be easily inserted into the cochlea, and removed and reinserted, if required; (4) it focuses or directs the current density towards the target tissue through the use of specially-shaped or coated electrode contacts; and (5) it allows a desired drug or compound to diffuse into the tissue associated with the target area, thereby facilitating a desired treatment of the tissue, e.g., inhibition of fibrous tissue or bone growth, promotion of tissue healing, prevention of neural degeneration, or promotion of neural regeneration.

BRIEF DESCRIPTION OF THE DRAWINGS

The above and other features and advantages of the present invention will be more apparent from the following more particular description thereof, presented in conjunction with the following drawings wherein:

FIG. 1 depicts an electrode array and associated lead for attachment to an implantable cochlear stimulator in accordance with the present invention;

FIG. 2 illustrates a side view of the proximal end of the lead of FIG. 1;

FIG. 3A is a sectional view taken along the line 3A—3A of FIG. 3;

Corresponding reference characters indicate corresponding components throughout the several views of the drawings.

DETAILED DESCRIPTION OF THE INVENTION

Figure 3:
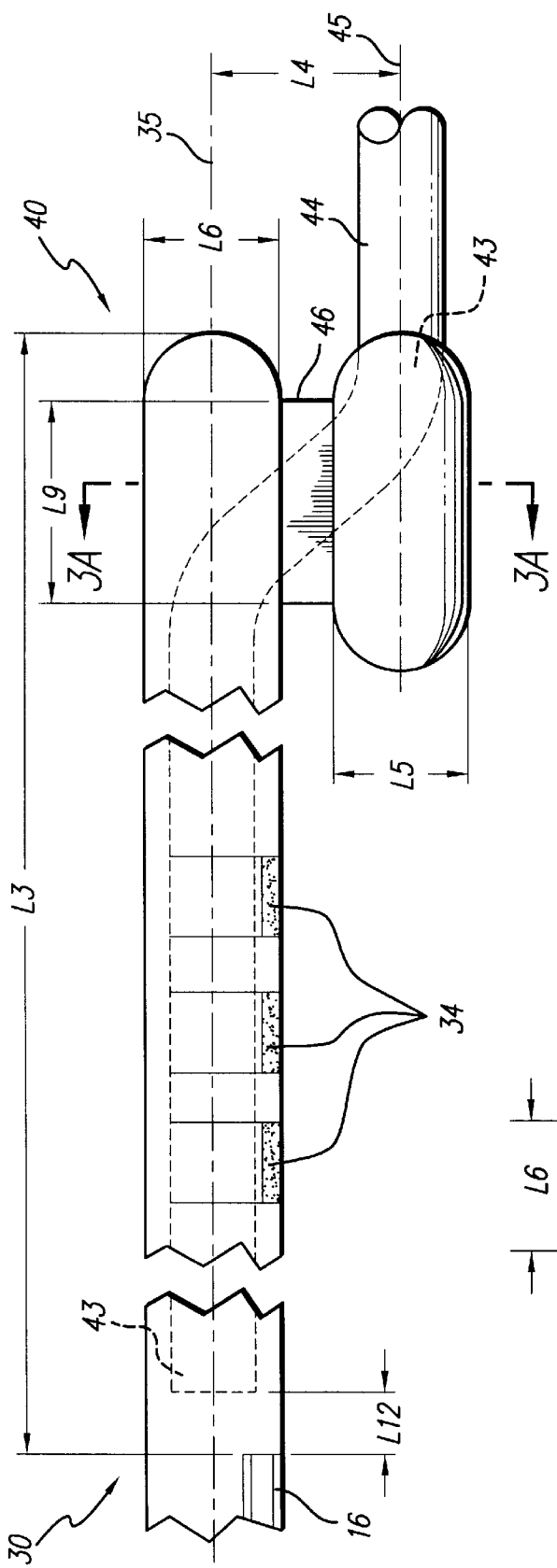
FIG. 3 is a more detailed view of the offset portion of the lead/array of FIG. 1.

The following description is of the best mode presently contemplated for carrying out the invention. This description is not to be taken in a limiting sense, but is made merely for the purpose of describing the general principles of the invention. The scope of the invention should be determined with reference to the claims.

It is to be understood that the teachings of the invention relating to providing current-focusing and tissue-treating features of a cochlear electrode array may be used with almost any type of cochlear electrode array, as well as many other types of implantable electrode arrays, e.g,. spinal column electrode arrays. The invention, however, will be described in connection with a description of the preferred cochlear electrode array, e.g., a modiolus-hugging, cochlear electrode array having its electrode contacts positioned on a medial side of the array.

The invention described herein teaches a particular type of implantable electrode array having multiple, electrode contacts. In a preferred embodiment, all of the electrode contacts have an exposed surface which, more or less, lies on the same side—the medial side—of the curved electrode. Further in a preferred embodiment, the electrode contacts are shaped or coated to control the surface impedance so as to focus or steer the current in a desired direction towards the target tissue. Additionally, in a preferred embodiment, the electrode contacts, and/or the entire electrode array, may optionally be coated with a suitable compound or other substance, i.e., a drug, that promotes a desired characteristic or inhibits an undesirable characteristic of the tissue at or near the target area.

The electrode array of the present invention may be best used with an implantable multichannel pulse generator, e.g., an implantable cochlear stimulator (ICS) of the type disclosed in U.S. Pat. No. 5,603,726, incorporated herein by reference, or other suitable stimulator. It is to be understood, however, that although a cochlear electrode array is hereafter described, having dimensions suitable for insertion into the cochlea, the principles of the invention may be applied to other types of implantable leads for applications other than cochlear stimulation.

The electrode array of the present invention is particularly adapted to bend or flex in one direction, thereby making it suitable for insertion into a curved body cavity, such as the cochlea.

An important feature of the electrode array of the present invention is that all of the active electrode contacts of the array are generally positioned along one side, e.g., the medial side (the inside of the curve or bend), of the array. Thus, when inserted into the curved or spiraling cochlea, which may advantageously be either a left or right cochlea, wherein the cells to be stimulated are located within the center modiolus wall, the electrode contacts are positioned proximate the modiolus wall, where they are closest to the cells to be stimulated. Hence, the electrode array of the present invention facilitates stimulation of the desired cells at lower power levels than would otherwise be needed if the electrode contacts were not proximate the modiolus wall.

Another feature of the electrode array of the present invention is that the electrode contacts have, in the preferred embodiment, a relatively large exposed electrode surface area that is generally planar or flat having a desired geometric shape, e.g., rectangular, semicircular, oval, star, or other shape. However, it is to be understood that the principles of the invention may also be practiced with electrodes that have exposed surface areas that are not flat, e.g., dimpled, or corrugated, or pitted.

Except as noted herein, the materials from which the electrode array of the invention is made, and the manner of making the electrode array, may be conventional, as are known in the art.

A preferred electrode array 30 in accordance with the present invention is shown in FIG. 1. The electrode array 30 forms the distal end of a lead/array assembly 40 adapted to be connected to an implantable cochlear stimulator (ICS), not shown. The lead/array assembly 40 includes the electrode array 30, a fantail proximal connector 42, and a lead body 44 connecting the array 30 to the proximal connector 42. The ICS is typically housed within a ceramic or other case, such as is disclosed in U.S. Pat. No. 4,991,152, incorporated herein by reference. The case has an array of feedthrough terminals corresponding to its multiple channels. A preferred ICS has eight channels, with each channel having two feedthrough terminals connected thereto. Such terminals are typically labeled as M1 and L1 (for medial and lateral) for the first channel, M2 and L2 for the second channel, and so on, up to and including M8 and L8 for the eighth channel.

The feedthrough terminals are spaced across a header of the case. Inside the case, each feedthrough terminal is connected to appropriate electronic circuitry for the corresponding channel, as taught in the previously-referenced '726 patent. On the outside of the case, each feedthrough terminal is connected to a corresponding wire conductor within the lead/array assembly 40. Such wire conductors are identified in FIG. 1 by the numbers 1 through 16. The wire conductors 1–16 are of necessity spread out at the point where they connect to the feedthrough terminals of the header. Thus, the proximal end of the lead/assembly 40 includes the fantail connector 42 that funnels the spread conductors 1–16 at the point they connect to the feedthrough terminals down to the lead body 44. A side view of the fantail connector 42 is shown in FIG. 2.

The manner of forming the fantail connector 42, and connecting it to the feedthrough terminals may be convenutal, and does not form part of the present invention. Rather, the present invention is directed to the electrode array 30 at the distal end of the lead/assembly 40. It should be emphasized that the electrode array 30 is not limited to use with a proximal fantail connector 42 and the type of ICS disclosed in the '726 patent. Rather, the electrode array 30 may be used with any type of proximal connector that interfaces with an appropriate pulse generator.

As seen in FIG. 1, the electrode array 30 is preferably curved an appropriate amount. A multiplicity of in-line electrode contacts 32 are spaced apart so as to lie on the medial side (inside of the curve) of the array. Sixteen such electrode contacts 32 are used in a preferred embodiment of the array 30. These electrode contacts are respectively connected to the wire conductors 1–16 within the lead. As shown in FIG. 1, the most distal electrode contact is connected to wire conductor 1 within the lead 44, which in turn is connected to the feedthrough terminal L1 at the pulse generator. The second-most distal electrode contact is connected to wire conductor 2 within the lead 44, and is connected to the feedthrough terminal M1 at the pulse generator. In this manner, the two-most distal electrode connectors 32 on the array may be connected to the first channel of the implantable pulse generator. In a similar manner, the two most proximal electrode contacts on the array 30 are connected to wire conductors 15 and 16 within the lead 44, and are connected to feedthrough terminals L8 and M8, corresponding to the eighth channel, of the implantable pulse generator. The other electrode contacts 32 included within the array 30 are similarly connected to a corresponding channel within the pulse generator.

As further seen in FIG. 1, the preferred electrode array 30 also includes three reference electrode contacts 34, identified in FIG. 1 by the electrode numbers 17, 18 and 19. Such reference contacts 34 are not connected to any wire conductors within the lead 44, and for this reason are sometimes referred to as "dummy reference contacts". Rather, each of these reference contacts 34 may provide a reference indicator or marker to the physician inserting the electrode array relative to the depth of insertion.

As also seen in FIG. 1, the lead/array assembly 40 further includes an offset portion 46 that effectively marks the end of the lead 44 and the beginning of the electrode array 46. Such offset portion 46 facilitates insertion of the electrode array 30 into the scala tympani duct of the cochlea. The insertion process may be conventional, and is aided by a special tool of the type disclosed in the '493 patent, previously referenced.

Turning next to FIG. 3, there is shown a more detailed view of the offset portion 46 of the lead/array 40. A sectional view of the offset portion 46, taken along the line 3A—3A of FIG. 3, is shown in FIG. 3A. As seen in these figures, the offset portion 46 separates the body of the lead 44 from the body of the array 30 by an offset distance L4. When measured from a center-line longitudinal axis 45 of the lead 44 to a center-line longitudinal axis 35 of the array 30, this distance L4, in the preferred embodiment, is about 1.3 mm. At the point of the offset, the diameter of the lead 44 is a distance L5, while the diameter of the electrode array is a distance L6. In the preferred embodiment, both L5 and L6 are about 0.8 mm. The length L9 of the offset portion 46 is approximately 1.6 mm, allowing the wire conductors 1–16 within the electrode array 30 to transition to the lead body 44 without too sharp of a bend. It is to be understood that these dimensions, as well as other dimensions presented herein, are only exemplary of one embodiment, and are not meant to be limiting.

Typically, as seen in FIG. 3, the body of the lead 44 may be made from a silicone rubber tube 43 that is inserted into the proximal end of the electrode array 30 up to a specified distance L12 from the first active electrode contact 16. In the preferred embodiment, L12 is approximately 3.0 mm, and the outer diameter of the tube 43 is approximately 0.64 mm. What this means, as a practical manner, as will become evident from the description below, is that the distal end of the tube 43 is positioned a distance L12 from the electrode contact 16 when the electrode array 30 and offset portion 46 are formed through a molding process.

The material from which the lead/array 40, including the electrode array 30, is made may be any suitable biocompatible material commonly used with implantable leads and other implantable components as is known in the art. A suitable material, for example, is a type of silicone polymer or rubber known as LSR-70 or LSR-25. The properties of LSR-70 and LSR-25 are well known in the art, and LSR-70 and LSR-25 may be obtained commercially from numerous sources, LSR-70 is formed into a desired shape by injecting or otherwise inserting it into a mold while in a liquid state and allowing it to cure in the mold at a specified temperature for a specified time period. For example, LSR-70 may cure at a temperature of 140 degrees C. for about 15 minutes. LSR-25 may likewise be formed into a desired shape using a similar molding process, or it may be applied through a suitable applicator, e.g., a syringe, to a desired area and then formed into a desired shape. LSR-25 is essentially the same as LSR-70 except that when it cures it is significantly softer, i.e., more pliable. Both LSR-70 and LSR-25 readily adhere to the tubing 43 so that when cured they become integral therewith.

Still with reference to FIG. 3, it is seen that the distance from the proximal end of the electrode array 30 to the proximal edge of electrode contact 16 (i.e., the electrode contact 32 that is connected to wire conductor 16) is a distance L3. In the preferred embodiment, the distance L3 is about 10.5 mm.

Figure 4:
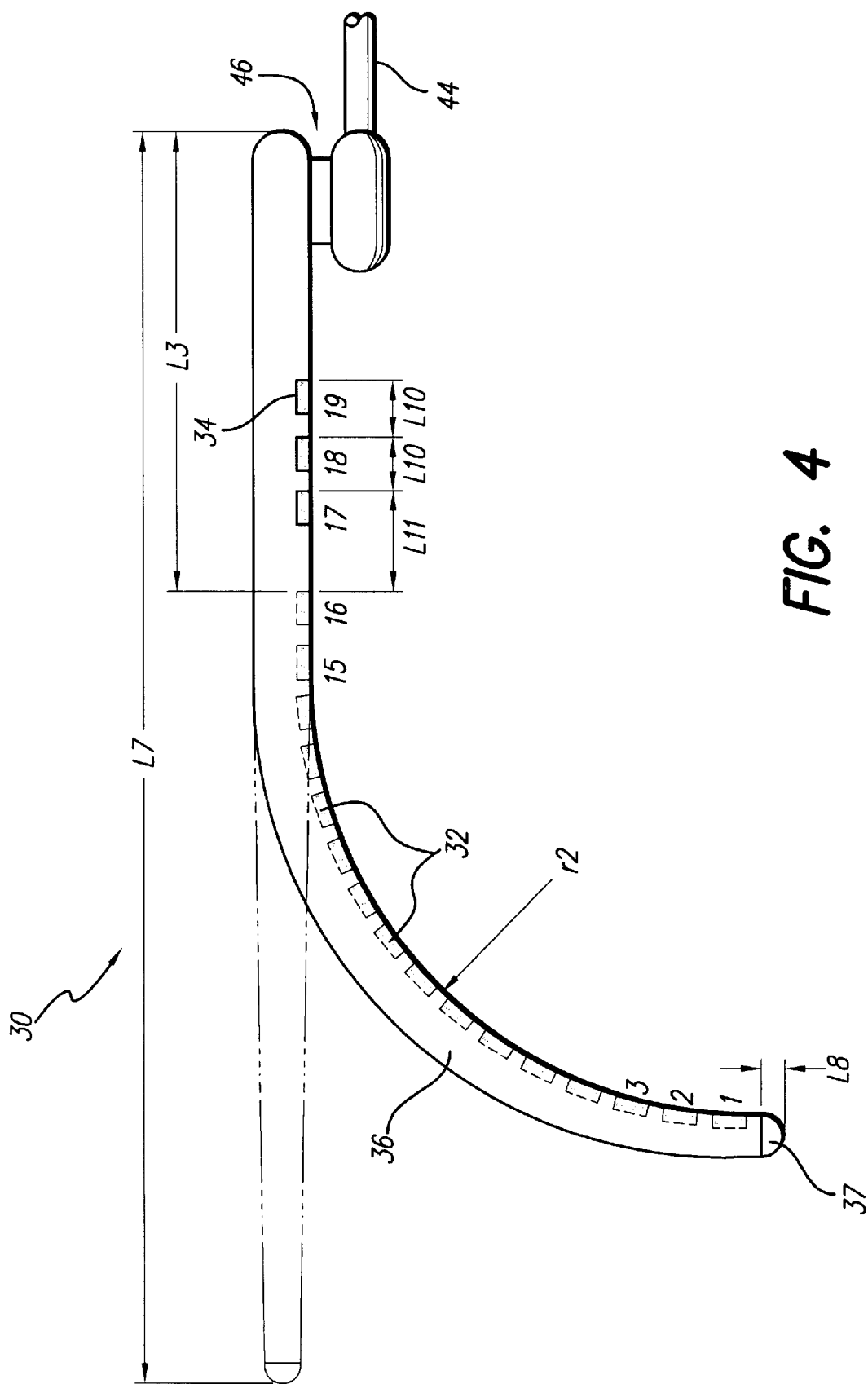
FIG. 4 shows the electrode array of the present invention having spaced-apart electrode array contacts along the medial side of the array, which electrode array comprises the distal end of the lead/array of FIG. 1.

Next, with reference to FIG. 4, a more detailed view of the electrode array 30 is shown. The electrode array includes electrode array contacts 32 equally-spaced along a medial side of a flexible carrier 36. The flexible carrier 36 is made from LSR-70, and is molded around an assembly of electrode contacts 32 and interconnecting wires as described below in conjunction with FIGS. 7A–11. The electrode array 30 has an overall length L7. Such length L7 is most easily measured when the array 30 is straightened, as shown by the dotted lines in FIG. 3. In the preferred embodiment, L7 has a value of approximately 25 mm. While the electrode array 30 could be formed to assume any desired shape, in the preferred embodiment it is formed to include a natural curve having a radius of curvature r2, with the electrode contacts 32 being positioned along the inside of the curve. The radius of curative r2 may have a value of approximately 9.0 mm.

As further seen in FIG. 4, a soft tip 37, having a depth of distance L8, is typically formed from LSR-25 at the very distal tip of the electrode array 30. In the preferred embodiment, L8 has a value of approximately 0.3 mm.

As additionally illustrated in FIG. 4, the reference marker contacts 34, identified as electrodes 17, 18 and 19, are spaced from the active electrode 16 a distance L11, with a spacing between the reference marker electrodes of L10. In the preferred embodiment, the distance L11 is about 3.0 mm, and the distance L10 is about 1.0 mm.

Figure 5:
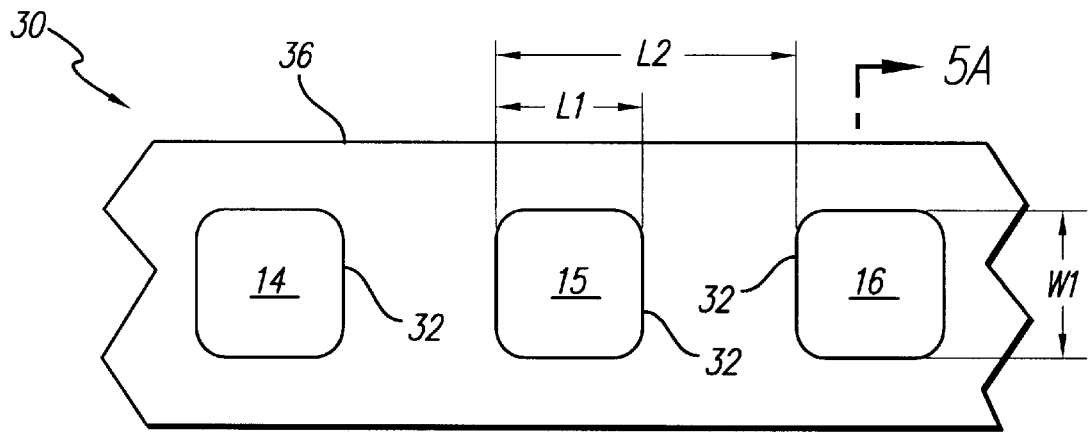
FIG. 5 shows a detail view of the electrode array contacts of the electrode array of FIG. 4.

Referring next to FIG. 5, the preferred spacing between the individual electrode contacts 32 is depicted. Such spacing, as well as all the other dimensional detail presented herein, is exemplary of a cochlear electrode, and is not intended to be limiting. As seen in FIG. 5, each exposed electrode contact surface area comprises a generally rectangular-shaped area having a length L1 and a width W1. Other shapes could also be used. In the preferred embodiment, the rectangular area is roughly a square, with L1 and W1 each having a value of approximately 0.4 mm±10%, thereby providing an exposed electrode surface area of approximately 0.16 $mm^2$. The spacing between corresponding points of adjacent electrode contact areas 32 is a distance L2. L2 has a nominal value of approximately 0.9 mm±0.1 mm.

Figure 5A:
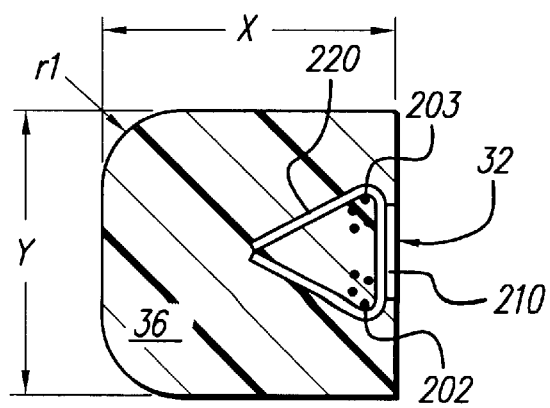
FIG. 5A is a sectional view of the electrode array taken along the line 5A—5A of FIG. 5.

The electrode contact areas comprise an exposed surface of an electrode contact 32 that is formed from folded strips 210 and 220 of a biocompatible metal, such as platinum, as described more fully below in conjunction with FIGS. 7A–8D. Such electrode contacts are embedded within the molded carrier 36 as illustrated in the sectional view of FIG. 5A, which is taken along the lines 5A—5A of FIG. 5. As seen in FIG. 5A, the carrier 36 is formed to have a cross-sectional area that is generally rectangular, having dimensions of X by Y mm, where the values of X and Y vary as a function of where along the length of the carrier the cross section is viewed. At electrode 16 (near the proximal end of the electrode/array 30), for example, X and Y are both about 0.8 mm. At electrode 1 (near the distal tip of the electrode array), X and Y are both about 0.6 mm. Thus, it is seen that the carrier 36 is tapered along its length so that it has a smaller cross section at its distal tip than it does at its proximal end.

Still with reference to the cross-sectional view of the array shown in FIG. 5A, it is seen that the sectional shape has rounded corners on the side opposite the medial side. (As explained previously, the medial side is the side where the electrode contacts 32 are located.) The rounded corners have a radius of curvature r1 that is approximately 0.3 mm in the preferred embodiment.

The electrode contacts 32 have a general cross sectional shape, as seen in FIG. 5A, and as will be more evident from the description below of FIGS. 7A–8D below, that resembles a triangle. The base of this triangular-shaped (or "Δ-shaped") electrode forms the exposed electrode contact area along the medial side of the electrode array, e.g., as seen in FIG. 5. The upward sloping legs 220 of this Δ-shape electrode extend into the body of the carrier, e.g., as anchors, and thus become embedded (non-exposed) portions of the electrodes. It should be noted that while in the preferred embodiment the upward sloping legs 220 touch at their respective tips to form the Δ shape, such touching is not required; nor is the Δ shape required. What is important is that these legs 220 extend into the body of the carrier, in some fashion, so that the electrode is firmly anchored in its desired position along the length of the array. For example, in some embodiments, the legs 220 may be completely folded over so as to lie almost flat on top of the exposed surface area, as shown generally in parent application (Ser. No. 09/140,034). In other embodiments, the legs 220 may extend more or less straight into the body of the carrier, forming a generally block "U" cross-sectional shape.

Wire bundles 202 and 203 pass through the corners of the Δ-shaped (or other-shaped) electrodes and become embedded within the molded carrier 36 when formed. As explained in more detail below, at least one wire from at least one of these wire bundles makes electrical contact with each active electrode. The wires that do not make electrical contact with an electrode contact are nonetheless engaged by or supported by the embedded portion of the electrode as they pass through the Δ (or other) shape. Such engagement helps support and position the wire bundles prior to molding the carrier over them. Moreover, the location of the wire bundles immediately behind and along opposing edges of the exposed surface area of the electrodes helps add additional stiffness to the electrode array, once formed, in the lateral direction, as explained below, thereby making it more difficult to bend or twist the array in the lateral direction. In contrast, the array remains relatively easy to bend in the medial direction. As used herein, the medial direction is the direction of curvature defined by the radius r2 (FIGS. 4 and 6).

Figure 6:
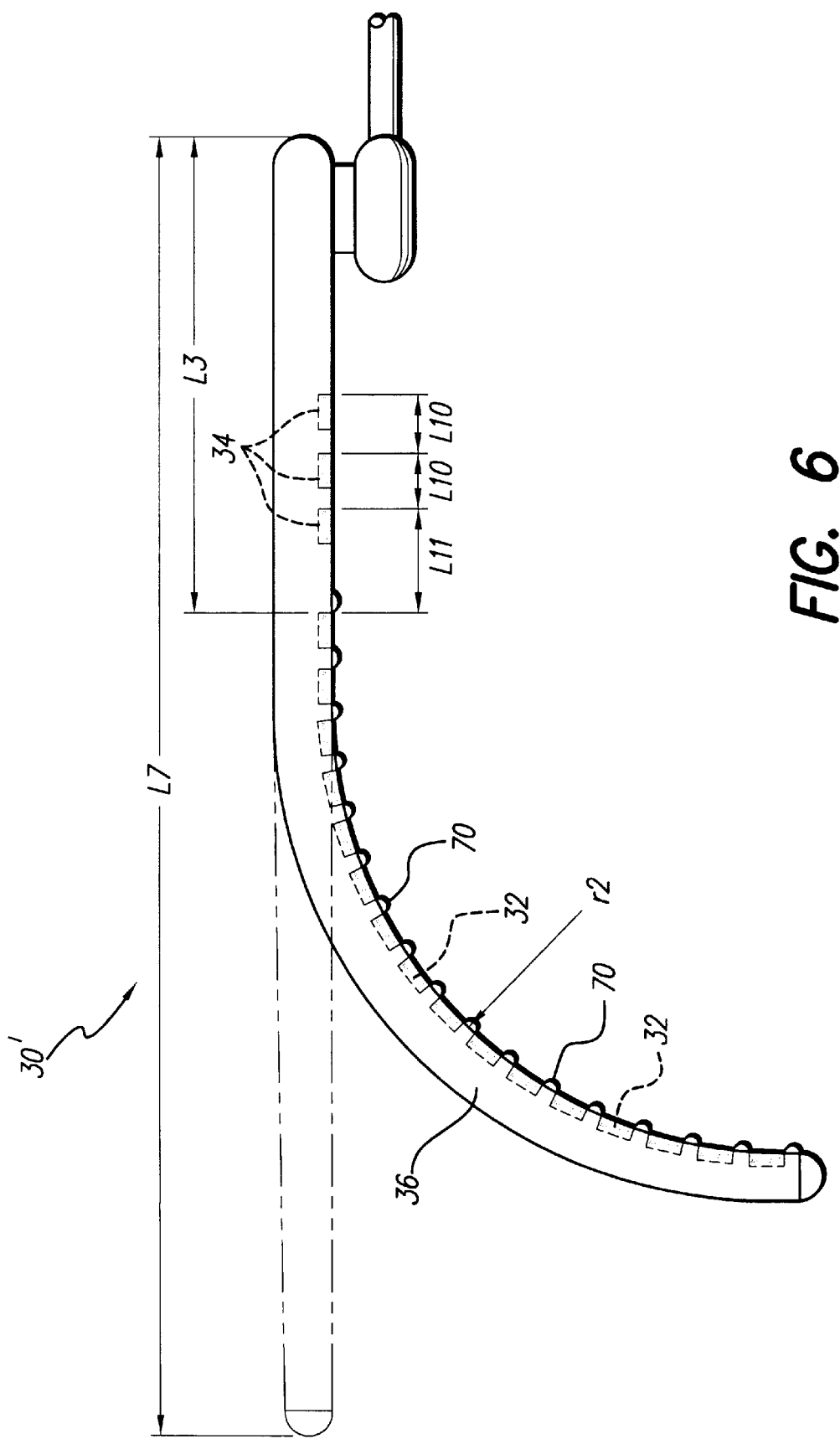
FIG. 6 shows an alternative embodiment of the electrode array of the present invention wherein bumps are formed in the space between each electrode contact.
Figure 6A:
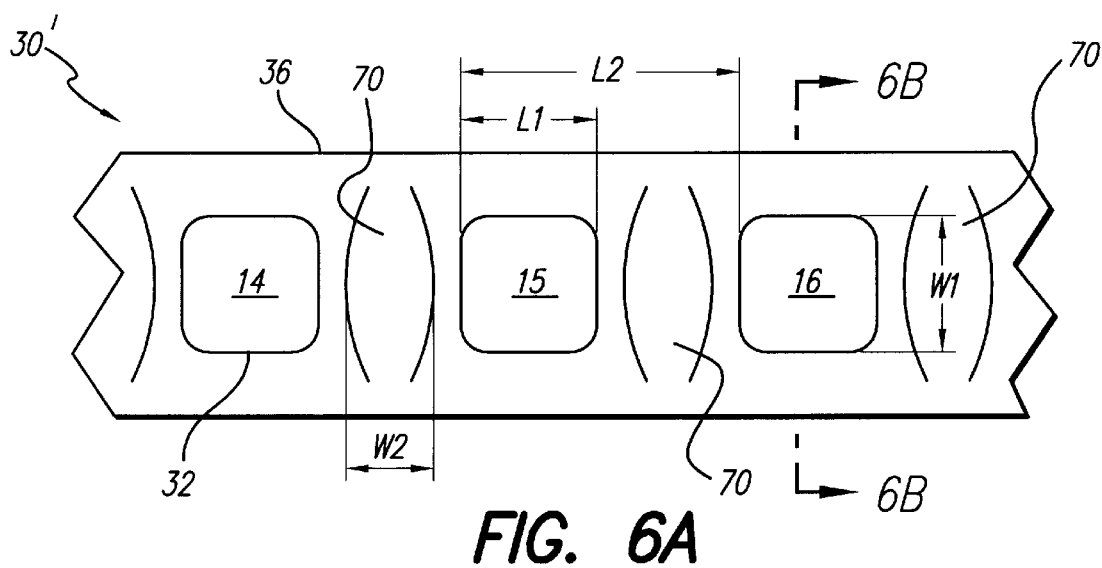
FIG. 6A shows a detail view of the electrode array contacts of the alternative electrode array of FIG. 6.
Figure 6B:
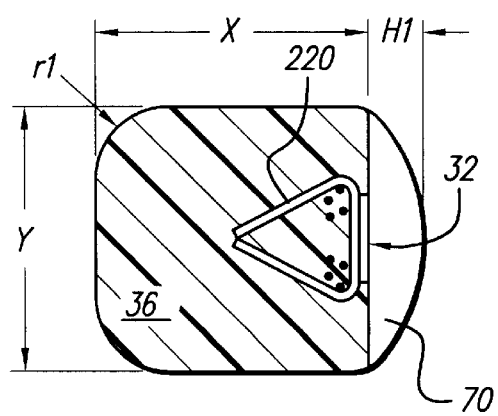
FIG. 6B is a sectional view of the alternative electrode array taken along the line 6B—6B of FIG. 6A.

An alternative embodiment an electrode array 30' made in accordance with the present invention is shown in FIGS. 6, 6A and 6B. This alternative electrode array 30' is the same as the array 30 illustrated in FIGS. 4, 5 and 5A with the exception that a series of small non-conductive bumps, or humps 70, are formed between the electrode contact areas 32. As seen best in FIG. 6B, these humps 70 have a height H1 of about 0.13 mm, and as seen best in FIG. 6A, have a width W2 of about 0.25 mm. As further seen best in FIG. 6, the humps 70 extend out from the medial surface of the electrode array. The humps 70 are made from a soft silicone rubber, or equivalent substance, such as LSR-25. When inserted into the cochlea, the small bumps 70 serve as non-irritating stand-offs, or spacers, that allow the electrode contacts 32 to be positioned near the modiolus wall, but prevent the electrode contacts 32 from actually touching the modiolus wall. The humps 70 further serve as dielectric insulators that help steer the stimulating electrical current, flowing to or from the electrode contacts, in the desired direction, from or towards the cells located in the modiolus wall, as taught, e.g., in the previously referenced copending U.S. patent application Ser. No. 09/137,033. Except for the presence of the humps 70, FIGS. 6, 6A and 6B correspond to FIGS. 4, 5 and 5A.

One of the advantages of the present invention is that the electrode array is easy and relatively inexpensive to manufacture. A preferred method of making the electrode array 30 or 30' is illustrated, for example, in FIGS. 7A through 11. It is to be emphasized that the method depicted in these figures of making the electrode array is not the only way an electrode array 30 or 30' could be made. However, it represents an easy and inexpensive (and thus a preferred) way to make the electrode array.

Most designs of electrodes and connectors are based on the principle of molding a contact or array of contacts, usually made from biocompatible metal, into a polymer carrier like silicone or polyurethane rubber. The electrode contacts are usually required to be located in a controlled position in reference to the surface of the carrier, with specified surface areas to be fully exposed to the stimulated or interconnection area. Disadvantageously, making such electrodes or connectors becomes extremely difficult, especially when the contacts are very small and/or a large number of contacts are required, e.g., as is the case with a cochlea electrode. One of the main problems encountered in the fabrication of such electrodes or connectors is to find a reliable method of holding the system of contacts in the desired and stable position during the process of welding the connecting wires and molding the polymer carrier. A further problem relates to maintaining a controlled surface of the contacts that are to remain exposed, i.e., to ensure that the contacts are not covered by the polymer when the carrier is molded.

The preferred methods of making the electrode array 30 or 30' described below in connection with FIGS. 7A through FIG. 11 are based on the principle of attaching (by the process of resistance welding) electrode contacts made from precious, biocompatible material (such as platinum or its alloys) to a foil carrier made from a non-toxic but chemically-active metal, such as iron (Fe). Resistance welding advantageously provides a secure attachment of the electrode material to the foil carrier without causing a deep fusion of the two materials being attached. The resulting shallow fusion contact, in turn, allows clean exposed electrode surface areas to be formed when the foil carrier is eventually chemically etched away, as explained below. Other types of attachment that result in shallow fusion of the electrode material and the foil carrier sheet material may also be used in lieu of resistance welding.

Attached to the metal carrier, the electrode contacts remain in a desired and stable position allowing easy connecting of the wiring system and subsequent molding of the polymer carrier. After completion of the molding process, the metal foil carrier is chemically etched away using a mixture of diluted acids, such as $HNO_3$ and HCl. The precious metal contacts and polymer are immune to the acid and remain in their intact, unaltered shape, and thereby provide the desired electrode array structure.

Figure 7A:
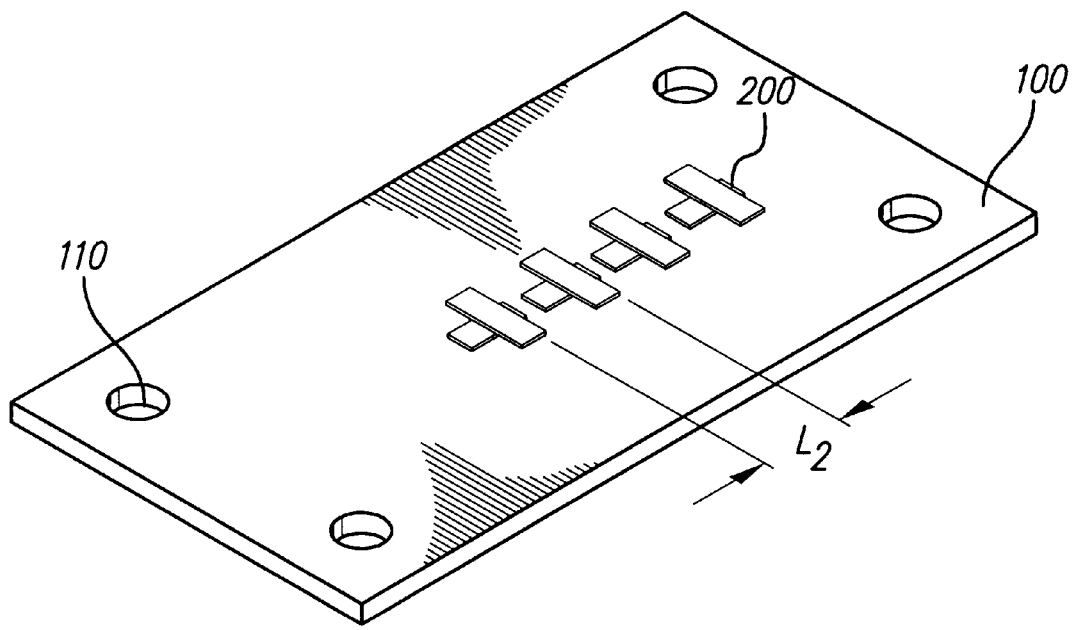
FIG. 7A depicts a preferred manner of making a multi-electrode contact array in accordance with the present invention.
Figure 7B:
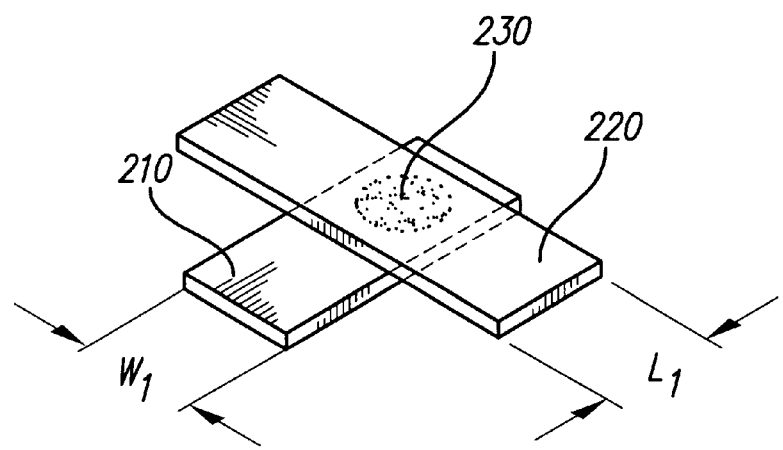
FIG. 7B shows an enlarged view the "T" strips used in making the electrode contacts of the array of FIG. 7A.

To illustrate the method, the method will be described relative to the fabrication of the electrode array 30 or 30' suitable for insertion into the cochlea. As a first step, an array of contacts 200 are resistance welded onto an iron carrier 100 so as to assume a desired in-line spaced-apart relationship, as shown in FIG. 7A. Each contact 200 consists of two pieces of platinum foil 210 and 220, connected together and joined to the carrier 100 by a shallow-fusion spot weld 230, as shown in FIG. 7B. The width of the strip 210 is approximately W1, and the width of the strip 220 is approximately L1. These strips are arranged to form a "T" shape, when viewed from a top view, with the strip 210 forming the leg of the "T", and with the strip 220 forming the cross bar of the "T". Moreover, the legs of each "T", are arranged in-line, with the proper spacing L2 therebetween, as shown in FIG. 7A.

As a second step, a wiring system is connected to each of the electrode contacts 200. This is accomplished as shown in FIGS. 8A, 8B, 8C and 8D. As seen in FIG. 8B, for example, an insulated wire 202', is laid on top of the electrode foil piece 220 (the cross bar of the "T"). The leg of the "T" of the foil piece 210 is then folded over to hold the end of the wire while the wire is welded in position (FIG. 8B). The welding process, preferably a resistance weld, burns away any insulation from the tip while making a secure mechanical and electrical connection between the wire and the electrode contact 200. The result is an electrode contact 200 having a wire 202' securely attached thereto (FIG. 8C). If other wires are present, e.g., going to more distal electrode contacts, then such wires may pass over the foil piece 210, lying more or less parallel to the wire 202' so as to form a bundle of wires 202. A similar bundle may be formed on the other side of the folded foil piece 210, thereby forming another wire bundle 203. The ends of the foil piece 220 are then folded upwards to form, in a preferred embodiment, a triangle, or Δ shape (as seen in a side view), as shown in FIG. 8D.

Figure 8A:
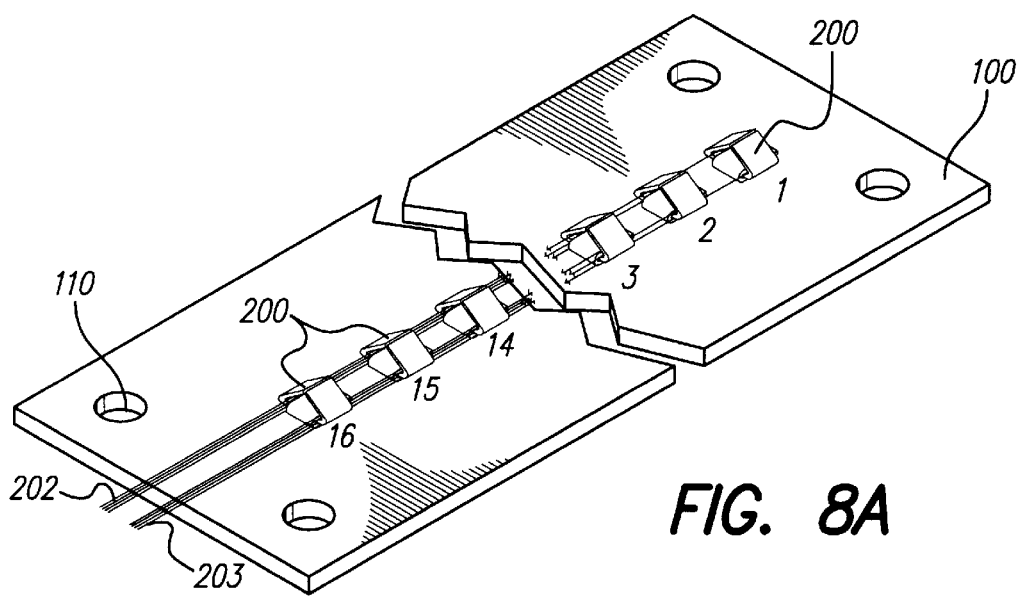
FIGS. 8A, 8B, 8C and 8D illustrate one manner in which wires are bonded and routed to each of the "T" strip electrode contacts of FIG. 7B during manufacture of the electrode array.
Figure 8B:
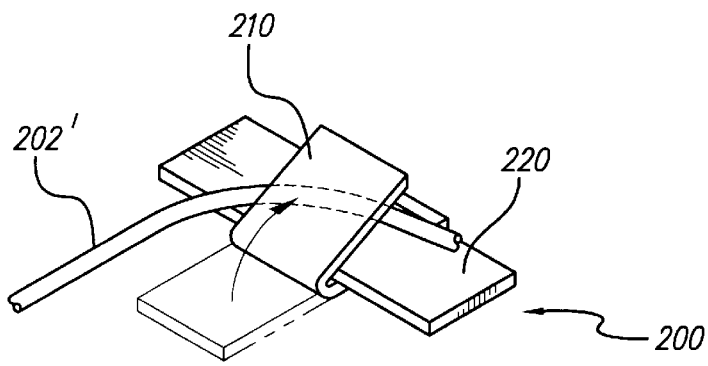
Figure 8C:
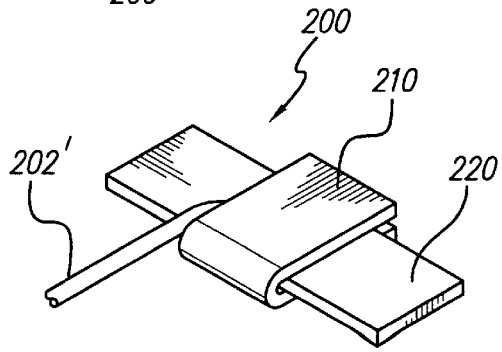
Figure 8D:
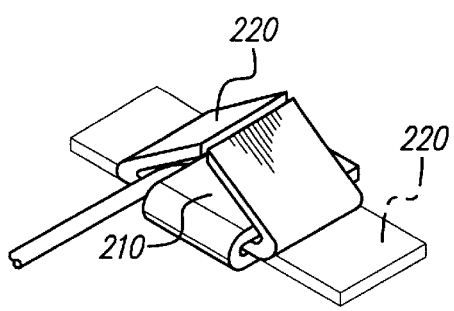

As seen in FIG. 8A, at least one wire from one of the bundles 202 or 203 is attached to the electrode contacts 2–16 in the manner described above. (For simplicity, only six of the sixteen or nineteen electrode contacts used in the electrode array 30 or 30' are shown in FIG. 8A,) Typically, a wire from wire bundle 202 will connect to electrode contact 16, and a wire from bundle 203 will connect to electrode contact 15, and so on, with adjacent in-line electrode contacts being connected to wires from alternating wire bundles. At least two wires, one from each bundle 202 and 203 remain for connection to the most distal electrode contact 1. In this fashion, at least seventeen wires are used to make electrical connection with sixteen electrode contacts. In the preferred embodiment, for example, the wire bundle 202 may contain 9wires, and the wire bundle 203 may contain 8wires, for the sixteen-electrode array 30 or 30' described herein. The wire bundles 202 and 203 pass through the dummy electrode contacts, or reference marker contacts 34 (FIGS. 1, 6), without making electrical contact therewith. For simplicity, the reference marker contacts 34 are not shown in FIG. 8A.

Having a wire bundle on each lateral side of each electrode contact, e.g., as seen in the sectional view of FIG. 5A or 6B, and hence on each lateral side of the electrode array, helps add lateral stability to the array. This is true even when the wire "bundle" only contains one wire. Thus, an important feature associated with using two wire bundles in the manner described is that the wire bundles help add stiffness to the electrode array in the lateral direction, but do not materially affect the ability of the array to flex or bend in the medial direction.

Figure 9:
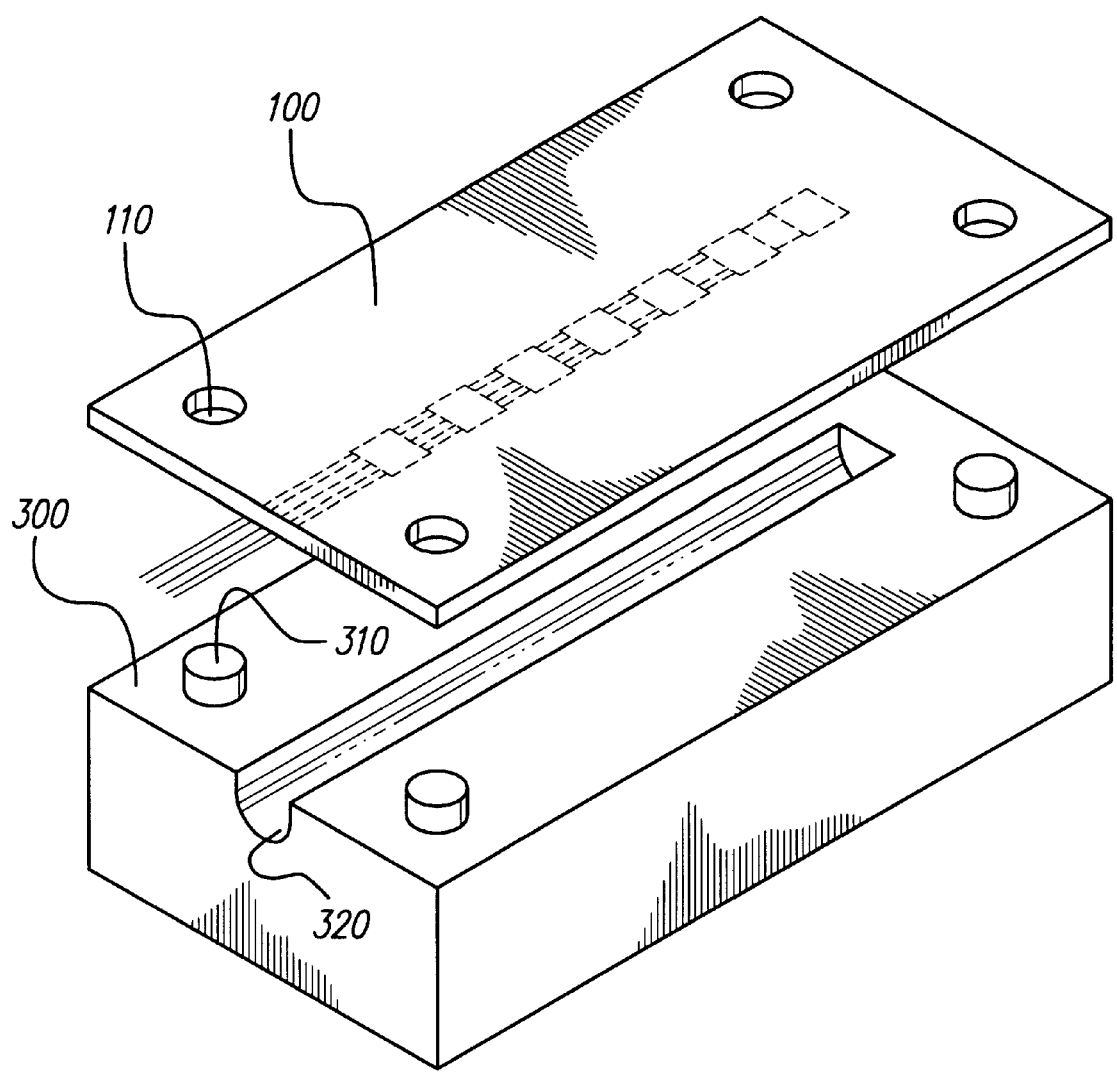
FIG. 9 depicts a molding die onto which the partially-formed electrode array of FIG. 7A, with wires attached to each of the electrodes as shown in FIGS. 8A–8D, may be mounted in order to form a straight polymer carrier for the electrode array.

Once the wire bundles 202 and 203 have been connected to all of the active electrodes 200, the foil carrier 100 may be placed on a molding die 300 as shown in FIG. 9. The die 300 has alignment pegs 310 adapted to align with corresponding alignment holes 110 in the foil carrier 100. The die 300 further has a cavity or channel 320 formed therein into which the required amount of material, e.g., LSR-70, needed to form the polymer carrier 36 (FIGS. 4, 6) is injected. The LSR-70 is then cured in conventional manner. This cavity or channel 320 may be shaped or formed as desired. The mold depicted in FIG. 9 would form a straight carrier 36.

Figure 10:
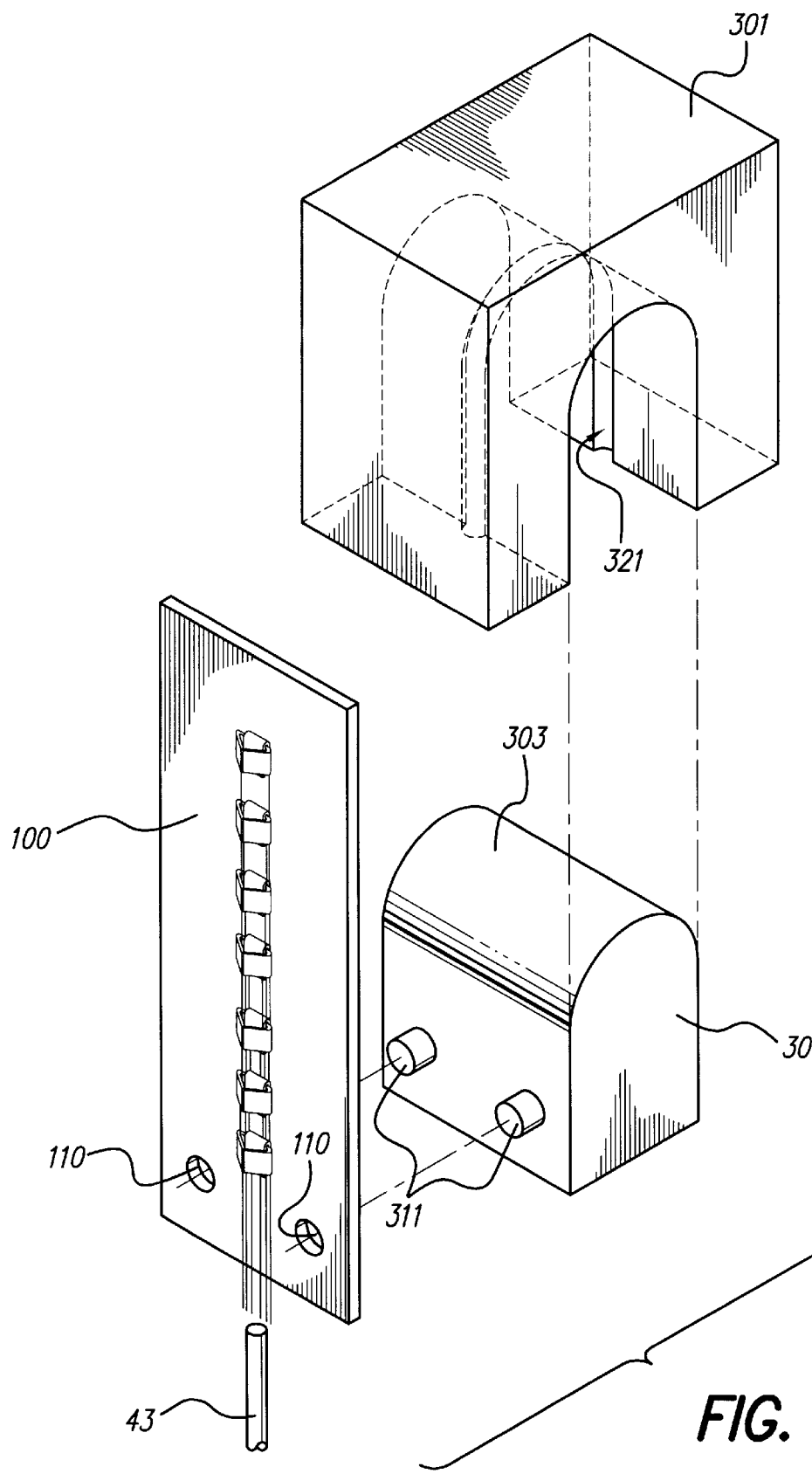
FIGS. 10 and 11 illustrate a perspective and side exploded view, respectively, of an alternative type of molding die onto which the partially-formed electrode array of FIG. 7A, with wires attached to each of the electrodes as shown in FIGS. 8A–8D, may be mounted in order to form a curved polymer carrier for the electrode array.
Figure 11:
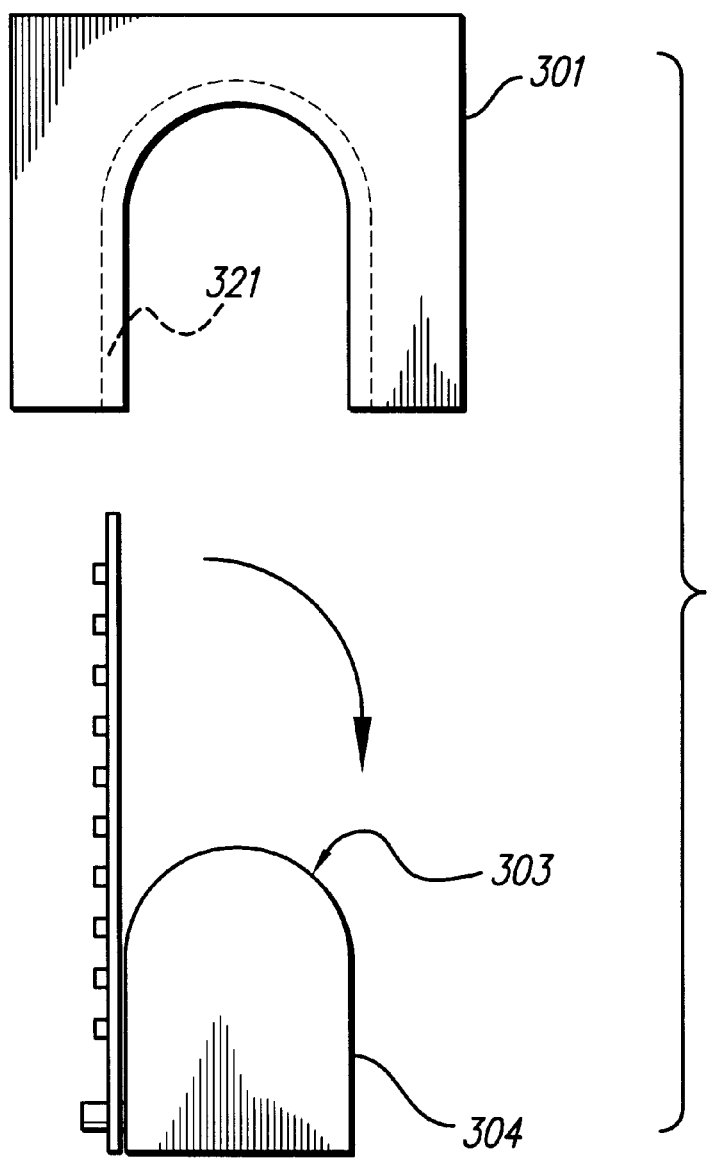

As an alternative to the flat-surface die 300 shown in FIG. 9, a curved die 301 is preferably used as shown in FIGS. 10 and 11. Such die 301 includes a curved surface 303 on a holding block 304 on which the foil carrier 100 may be placed. The block 304 has alignment pegs 311 adapted to align with corresponding alignment holes 110 in the foil carrier 100. The foil carrier 100 is placed on the block 304 and bent over the curved surface 303. The die 301 is then placed over the block 304, with the foil carrier 100 sandwiched therebetween. A channel or cavity 321 is formed in the die 301 having the desired shape and characteristics of the carrier that is to be formed through the molding process. The required amount of material to form the polymer carrier 36, e.g., LSR-70, is then injected into the channel and allowed to cure. By placing the foil carrier assembly 100 in the curved die of FIGS. 10 and 11 (note that FIG. 10 comprises a perspective view of the die 301 and block 304, and FIG. 11 comprises a side or profile view of the die 301 and block 304), the array can be molded or formed to assume the desired curved shape. Such curved shape is preferred to achieve directional stability of the array during insertion.

Thus, it is seen that through proper use of the die 300 or 301/304, or other dies, the electrode array may be formed to assume a natural curved shape, a slightly curved shape, or to be straight.

After the material used to form the carrier (e.g., LSR-70) cures, the foil carrier with the electrode array assembly (which is now molded inside of the polymer) is removed from the channel of the die 300 or 301/304 and placed in a mixture of diluted acids. The mixture of diluted acids dissolves the foil carrier 100, thereby exposing a clean surface of the electrode contacts 200. After washing to remove any residue of acids and Fe salts, the main electrode array structure is completed.

Advantageously, the structure of the electrode array 30, as seen best in the sectional view of FIG. 5A, or the electrode array 30', as seen best in the sectional view of FIG. 6B, bends or flexes more easily in the medial direction than in the lateral direction. That is, the electrode array, with its slight curved shaped, when inserted into the cochlea, is able to bend, as required, to follow the scala tympani duct of the cochlea (whether the right or left cochlea) as it is inserted deeper and deeper into such duct. As it does so, the electrode contacts 32 remain closest to and facing the modiolus wall, as desired. As the electrode array is inserted deeper into the cochlea, the electrode array does not easily twist, or bend laterally, which twisting or bending could move the electrode contacts away from the modiolus wall. This is because the electrode array is inherently stiffer in the lateral direction than in the medial direction due primarily to the presence of the wire bundles and folded/bent electrode contacts which provide an added degree of stiffness in the lateral direction.

Figure 12A:
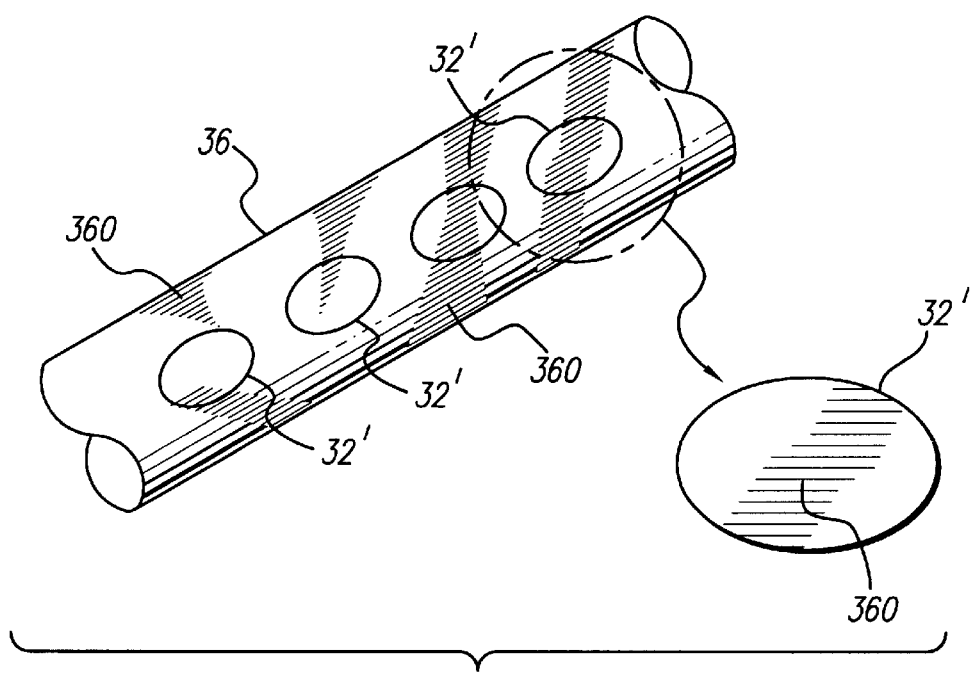
FIGS. 12A and 12B illustrate representative electrode contact shapes.
Figure 12B:
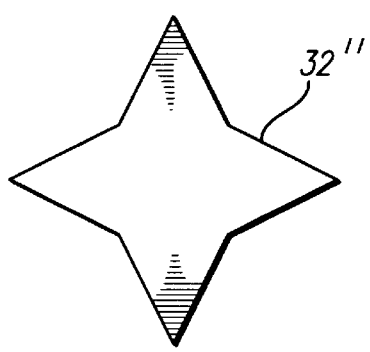

Turning next to FIGS. 12A and 12B, representative electrode contact shapes are illustrated. In FIG. 12A, the electrode contacts 32' are formed in an oval shape along one surface of flexible carrier 36. In FIG. 12B, the electrode contact 32" is configured in a star shape. Such shapes are only exemplary of many different shapes that the electrode contacts may assume. The shape is selected as an aid to control the current flow and current density associated with the electrode contact as a function of position on the electrode contact. That is, the shape or geometry of the exposed electrode contacts 32' or 32" is designed to diminish the surface of the electrode contact at the outside edges of the contact, thereby focusing most of the current to flow through the center of the electrode contact.

Figure 13A:
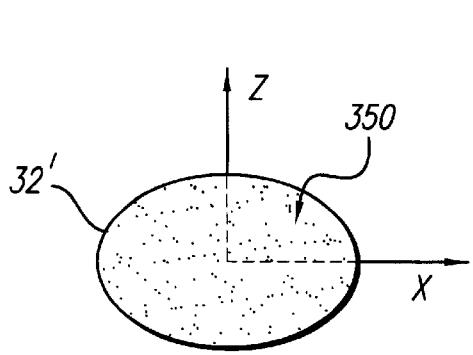
FIG. 13A depicts an electrode coated with a dielectric that controls the surface contact impedance Z.
Figure 13B:
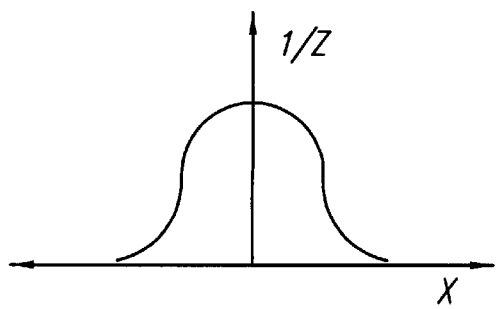
FIG. 13B illustrates the manner in which the inverse of the impedance (1/Z) varies relative to the center location of the electrode illustrated in FIG. 13A.

In another embodiment, shown in FIG. 13A, the electrode contact 32' is coated with a dielectric 350 or other material that controls the surface contact impedance Z so that the impedance increases as a function of distance from the center of the electrode, X. That is, the coating 350 (represented in FIG. 13A by random dots), is controlled in an appropriate fashion, e.g., by controlling its thickness, so that the impedance is lowest (or the inverse of the impedance, 1/Z, is highest, as shown in FIG. 13B) near the center of the electrode contact. This has the effect of focusing most of the current flow through the center of the electrode contact.

Figure 14:
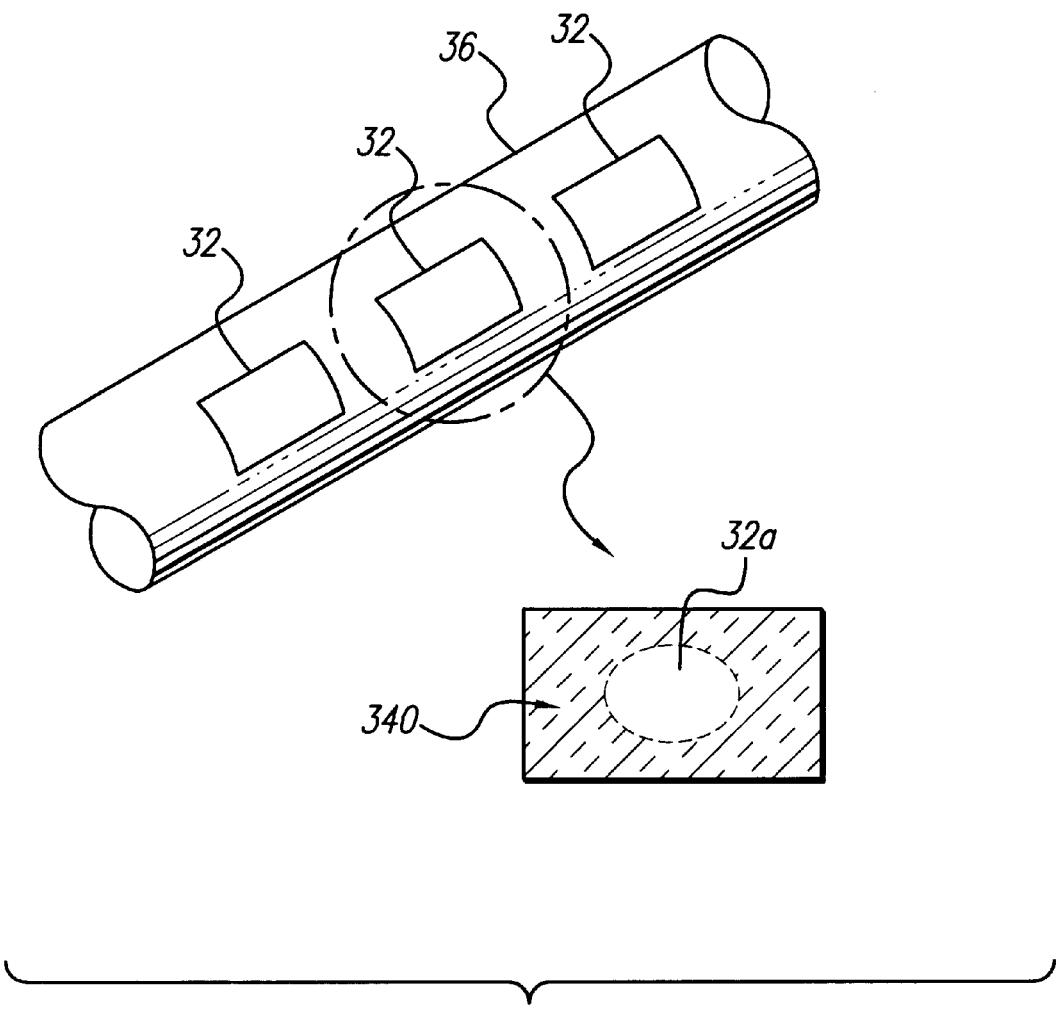
FIG. 14 shows an electrode wherein the exposed electrode contact surface area is masked with a suitable insulator to prevent conduction of current at various locations on the exposed surface.

In yet a further embodiment, shown in FIG. 14, the exposed electrode contact surface area 32 is masked with a suitable insulator 340 to prevent conduction of current at various locations at the electrode contact edge or at other areas on the exposed surface. For example, as seen in FIG. 14, a mask 340 is placed over the rectangular-shaped electrode contact 32, where the mask covers all of the electrode contact except for an oval-shaped area 32a in the center of the electrode contact. The insulator mask 340 may be formed to permit current flow through any desired unmasked area or regions of the electrode contact surface, thereby allowing the current flow to be better focused at the target tissue.

The shapes or geometries of the electrode contacts may be formed using any suitable technique. One technique is to form pieces of the desired shaped electrodes from a precious, biocompatible material (such as platinum or its alloys) and attach such shaped electrode pieces to a foil carrier made from a non-toxic but chemically-active metal, such as iron (Fe). The first and second metal strips 210 and 220 (FIG. 7B) may then be placed over the shaped electrode piece and resistance-welded thereto. The process of making the electrode then proceeds as described above in connection with FIGS. 7A–11. Resistance welding advantageously provides a secure attachment of the electrode material to the foil carrier without causing a deep fusion.

As an additional feature of the invention, the surface of the electrode contacts 32, 32', or 32", and/or the flexible carrier 36, may be coated with a suitable drug compound 360, as illustrated in FIG. 12A. When the electrode array is implanted, the drug compound 360 diffuses into the tissue and liquids surrounding the electrode array. Advantageously, the drug compound 360 is selected to elicit a desired result, e.g., to inhibit fibrous tissue or bone growth in the vicinity of the electrode contacts; or to promote the healing of damaged tissue in the region of the electrode contacts.

In the preferred embodiment, the coating 360 is placed on the carrier 36 and/or electrode contacts 32, 32' or 32" prior to insertion of the electrode array into the scala tympani (or other tissue location). However, it should be noted that additional substances or drug compounds may also be delivered through a delivery channel that forms part of the electrode array, as taught, e.g., in applicant Kuzma's previously-referenced copending United States Patent Application, entitled "Cochlear Electrode With Drug Delivery Channel, and Method of Making Same" (Attorney Docket No. AB-065U).

Representative substances or drug compounds 360 that may be used to coat the electrode array and/or the individual electrode contacts include selected steroids, either naturally-occurring steroids or synthetic steroids. Additionally, the selected drug compound 360 may comprise a Neuro-trophin selected to prevent neural degeneration and/or to promote neural regeneration.

As described above, it is thus seen that the present invention provides an electrode array that is easy to manufacture and which provides enhanced performance when used. Such electrode array provides an array of spaced-apart electrodes along the medial side of the array. The electrode contacts are shaped or formed to help steer or focus the current flowing through the electrode contact to or from the target tissue, e.g., by increasing the impedance at the edges of the contact and decreasing the impedance at the center of the contact. Additionally, the electrode contacts, or the entire electrode array, may be coated with a beneficial drug, or other compound, that promotes a desired result or condition in the target tissue, and/or inhibits an undesirable result.

As also described above, it is seen that upon insertion into the cochlea, the electrode contacts advantageously all face the modiolus wall. The composition and makeup of the electrode array makes it easier to bend in the medial direction than in a sideways or lateral direction. Thus, the electrode contacts remain on the medial side of the electrode, which medial side remains closest to the modiolus wall when the electrode is inserted into the cochlea.

While the invention herein disclosed has been described by means of specific embodiments and applications thereof, numerous modifications and variations could be made thereto by those skilled in the art without departing from the scope of the invention set forth in the claims.

What is claimed is:

1. An implantable electrode array for use with a tissue stimulation device comprising
    a flexible carrier;
    a multiplicity of electrodes having an exposed surface area;
    a multiplicity of wires embedded within the flexible carrier, at least one wire of the multiplicity of wires being electrically connected to a respective electrode; and
    a coating that covers at least a portion of the exposed surface area of the multiplicity of electrodes, wherein said coating controls the impedance of the exposed surface area as a function of distance from a center of the exposed surface area.

2. The implantable electrode array of claim 1 wherein the coating increases the impedance as a function of distance from the center of the exposed surface area.

3. An implantable electrode array for use with a tissue stimulation device comprising
    a flexible carrier;
    a multiplicity of electrodes having an exposed surface area;
    a multiplicity of wires embedded within the flexible carrier, at least one wire of the multiplicity of wires being electrically connected to a respective electrode; and
    a mask that covers at least a portion of the exposed surface area with an insulative material, said mask preventing conduction at various locations of the exposed surface area.

4. The implantable electrode of claim 3 wherein the mask prevents conduction around an edge of the exposed surface area.

5. An implantable electrode array for use with a tissue stimulation device comprising
    a flexible carrier;
    a multiplicity of electrodes having an exposed surface area;
    a multiplicity of wires embedded within the flexible carrier, at least one wire of the multiplicity of wires being electrically connected to a respective electrode;
    a drug coating that covers a portion of at least one of the exposed surface area or flexible carrier, the drug coating comprising a compound that diffuses into tissue surrounding the electrode array when the electrode array is implanted in the tissue, wherein the drug coating provides at least one of the following functions: inhibit fibrous tissue growth, inhibit bone growth, promote healing, prevent neural degeneration, or promote neural regeneration; and
    a second coating that controls the impedance of the exposed surface area as a function of distance from a center of the exposed surface area.

6. The implantable electrode array of claim 5 wherein the drug coating comprises a steroid.

7. The implantable electrode array of claim 5 wherein the drug coating comprises a neuro-trophin.

8. The implantable electrode array of claim 5 wherein the second coating causes the impedance to increase as a function of distance from the center of the exposed surface area.

9. An implantable electrode array for use with a tissue stimulation device comprising
    a flexible carrier;
    a multiplicity of electrodes having an exposed surface area;
    a multiplicity of wires embedded within the flexible carrier, at least one wire of the multiplicity of wires being electrically connected to a respective electrode;

a drug coating that covers a portion of at least one of the exposed surface area or flexible carrier, the drug coating comprising a compound that diffuses into tissue surrounding the electrode array when the electrode array is implanted in the tissue, wherein the drug coating provides at least one of the following functions: inhibit fibrous tissue growth, inhibit bone growth, promote healing, prevent neural degeneration, or promote neural regeneration; and a mask that covers at least a portion of the exposed surface area with an insulative material, said mask preventing conduction at various locations of the exposed surface area.

10. An implantable electrode array for use with a tissue stimulation device comprising a flexible carrier;

a multiplicity of electrodes having an exposed surface area;

a multiplicity of wires embedded within the flexible carrier, at least one wire of the multiplicity of wires being electrically connected to a respective electrode; and current-focusing means associated with the exposed surface area of each electrode for better focusing stimulation current flowing from or to the electrode at targeted tissue in the vicinity of the electrode when the electrode array is implanted in tissue and connected to the tissue stimulation device, wherein the current-focusing means comprises a geometric shape of the exposed surface area designed to vary current flow and current density as a function of position on the exposed surface area so as to focus most of the current flow through the center of the electrode contact.

11. The implantable electrode array of claim 10 wherein the geometric shape of the exposed surface area of each electrode comprises an oval shape.

12. The implantable electrode array of claim 10 wherein the geometric shape of the exposed surface area of each electrode comprises a star shape.

13. The implantable electrode array of claim 12 wherein the geometric shape of the exposed surface area of each electrode comprises a four-pointed star shape.

14. An implantable electrode array for use with a tissue stimulation device comprising a flexible carrier;

a multiplicity of electrodes having an exposed surface area;

a multiplicity of wires embedded within the flexible carrier, at least one wire of the multiplicity of wires being electrically connected to a respective electrode; and current-focusing means associated with the exposed surface area of each electrode for better focusing stimulation current flowing from or to the electrode at targeted tissue in the vicinity of the electrode when the electrode array is implanted in tissue and connected to the tissue stimulation device, wherein the current-focusing means comprises a dielectric layer disposed over at least a portion of the exposed surface area of each electrode for the purpose of affecting the contact impedance of the interface between the exposed surface area and surrounding tissue.

15. The implantable electrode array of claim 14 wherein the dielectric layer provides a lower contact impedance near the center of the exposed surface area of each electrode than at the edges of the exposed surface area, whereby most of the stimulating current flows through the center of the exposed surface area of the electrode.

16. An implantable electrode array for use with a tissue stimulation device comprising a flexible carrier;

a multiplicity of electrodes having an exposed surface area;

a multiplicity of wires embedded within the flexible carrier, at least one wire of the multiplicity of wires being electrically connected to a respective electrode; and current-focusing means associated with the exposed surface area of each electrode for better focusing stimulation current flowing from or to the electrode at targeted tissue in the vicinity of the electrode when the electrode array is implanted in tissue and connected to the tissue stimulation device, wherein the current-focusing means comprises a mask made from an insulative material that covers at least a portion of the exposed surface area of each electrode, wherein the mask prevents conduction at various locations on the exposed surface area of the electrode.

17. The implantable electrode array of claim 16 wherein the mask prevents conduction at the edges of the exposed surface area of each electrode, thereby focusing current flow to occur at the center of the exposed surface area of each electrode.

* * * * *